United States Patent
Liu et al.

(10) Patent No.: US 9,341,568 B2
(45) Date of Patent: May 17, 2016

(54) REFRACTIVE INDEX SENSOR FOR ANALYZING AN ANALYTE, AND METHOD OF FABRICATING THEREOF

(71) Applicant: AGENCY FOR SCIENCE, TECHNOLOGY AND RESEARCH, Singapore (SG)

(72) Inventors: Qing Liu, Singapore (SG); Jack Sheng Kee, Singapore (SG); Mi Kyoung Park, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 14/434,319

(22) PCT Filed: Oct. 8, 2013

(86) PCT No.: PCT/SG2013/000432
§ 371 (c)(1),
(2) Date: Apr. 8, 2015

(87) PCT Pub. No.: WO2014/058392
PCT Pub. Date: Apr. 17, 2014

(65) Prior Publication Data
US 2015/0268160 A1 Sep. 24, 2015

(30) Foreign Application Priority Data
Oct. 8, 2012 (SG) .............................. 201207483-7

(51) Int. Cl.
*G01N 21/41* (2006.01)
*G01N 21/55* (2014.01)
*G02B 6/10* (2006.01)

(52) U.S. Cl.
CPC ................ *G01N 21/41* (2013.01); *G01N 21/55* (2013.01); *G02B 6/10* (2013.01)

(58) Field of Classification Search
CPC ......... G01N 21/41; G01N 21/55; G02B 6/10; G01L 1/246
USPC .............. 356/128–137; 385/2, 12, 10, 37, 39, 385/129, 146
See application file for complete search history.

(56) References Cited

U.S. PATENT DOCUMENTS

| 5,071,248 | A | * | 12/1991 | Tiefenthaler | ......... | G01N 21/431 356/128 |
| 5,832,155 | A | * | 11/1998 | Rasch | ................ | G02B 6/12004 385/14 |
| 6,137,576 | A | * | 10/2000 | Pauluth | .................. | G01N 21/45 356/477 |

(Continued)

FOREIGN PATENT DOCUMENTS

WO 2014058392 A1 4/2014

OTHER PUBLICATIONS

Agency for Science, Technology and Research, "International Search Report and Written Opinion," dated Dec. 17, 2013, PCT App. No. PCT/SG2013/000432, 7 p.

*Primary Examiner* — Sang Nguyen
(74) *Attorney, Agent, or Firm* — Conley Rose, P.C.

(57) ABSTRACT

A refractive index sensor is provided for analyzing an analyte, the sensor including: a strip waveguide for receiving an input light signal therein and transmitting the light signal, subject to manipulation as it propagates through the strip waveguide, to a detector for analysis with respect to the analyte; and a slot waveguide for sensing the analyte disposed thereon and for receiving a sensing signal, corresponding to said manipulation of the light signal, from the strip waveguide, wherein a grating is formed on a surface of the strip waveguide to enable coupling of the sensing signal from the strip waveguide to the slot waveguide, and the sensor is configured with enhanced sensitivity based on a sensitivity difference between the slot waveguide and the strip waveguide, and/or a group index difference between the slot waveguide and the strip waveguide.

20 Claims, 11 Drawing Sheets

(56) References Cited

U.S. PATENT DOCUMENTS

| | | | | |
|---|---|---|---|---|
| 8,380,016 B1* | 2/2013 | Hochberg | ............ | G02F 1/2257 385/131 |
| 8,483,529 B2* | 7/2013 | Zhang | ................ | G02B 6/12002 385/122 |
| 8,798,414 B2* | 8/2014 | Quan | ................... | G02B 6/1225 385/10 |
| 2010/0310205 A1* | 12/2010 | Liu | ........................ | B82Y 20/00 385/2 |
| 2012/0012739 A1* | 1/2012 | Koch | ...................... | G01N 21/77 250/227.11 |
| 2013/0295688 A1* | 11/2013 | Bailey | .................. | C12Q 1/6804 436/501 |
| 2015/0131100 A1* | 5/2015 | Reck | ........................ | G01L 11/02 356/445 |

* cited by examiner

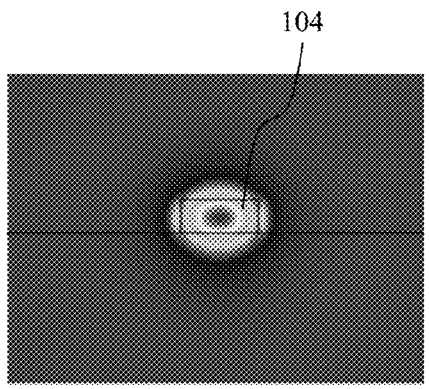
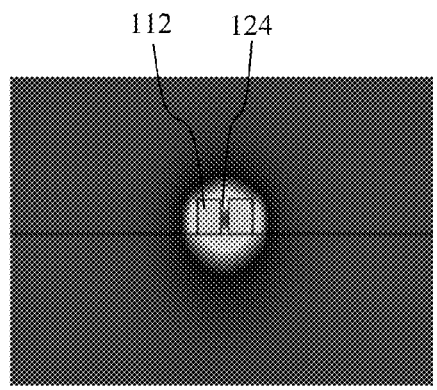
FIG. 3A
FIG. 3B
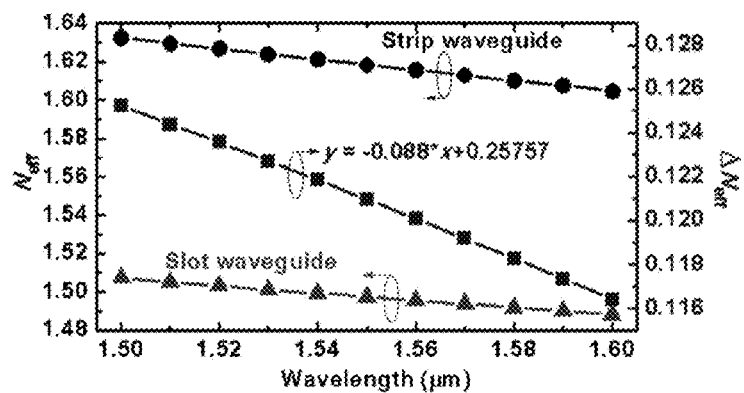
FIG. 3C
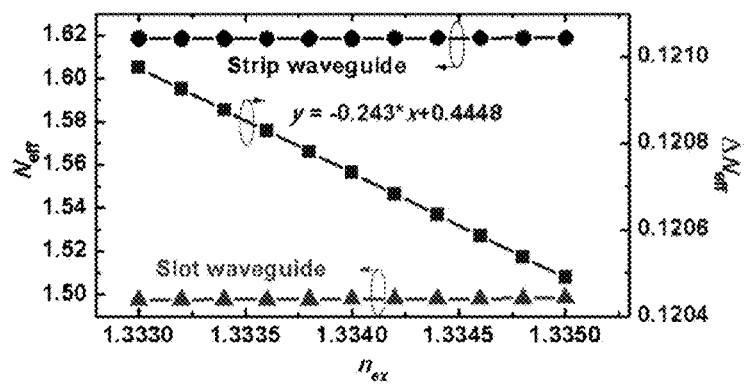
FIG. 3D

US 9,341,568 B2

REFRACTIVE INDEX SENSOR FOR ANALYZING AN ANALYTE, AND METHOD OF FABRICATING THEREOF

CROSS-REFERENCE TO RELATED APPLICATION

The present application is the U.S. National Stage under 35 U.S.C. §371 of International Patent Application No. PCT/SG2013/000432, filed 8 Oct. 2013, which claims priority to Singapore Application No. SG 201207483-7, filed 8 Oct. 2012, the disclosures of which are hereby incorporated herein by reference.

FIELD OF INVENTION

The present invention generally relates to a refractive index sensor for analyzing an analyte, such as in biochemical analysis, a method of fabricating the refractive index sensor, and more particularly, to a highly sensitive refractive index sensor.

BACKGROUND

Optical refractive index (RI) sensors have been extensively investigated for a number of applications and play a prominent role in biochemical analysis. Among the existing biochemical RI sensors, those based on integrated optical waveguides are of interest because of their high sensitivity, small size, and high scale integration. Recently, RI sensors based on certain types of slot waveguides have attracted interest due to their ability to provide high optical intensity in a subwavelength-scale low refractive index region (slot region). With such slot waveguides, larger light-analyte interaction in the slot region, and hence higher sensitivity, can be obtained as compared to conventional strip waveguides. Up to now, slot waveguide sensors based on ring resonator, Mach-Zehnder interferometer, Bragg grating, and directional coupler have been reported. The reported slot waveguide ring resonator sensors may exhibit sensitivity of about two times larger (about 212 nm/RIU (refractive index unit)) than that of ring resonator sensors based on conventional strip waveguides.

However, it would be beneficial to further enhance the sensitivity of the RI sensor to improve its analyte detection-measurement abilities in order to detectmeasure biomolecules with very low detection threshold for example. In addition, because of the complex nature of most biological interactions, it would also be beneficial to provide an RI sensor capable of wavelength multiplexed measurements.

A need therefore exists to provide a reflective index (RI) sensor for analyzing an analyte which is highly sensitive, and preferably also capable of wavelength multiplexed measurements. It is against this background that the present invention has been developed.

SUMMARY

The present invention seeks to overcome, or at least ameliorate, one or more of the deficiencies of the prior art mentioned above, or to provide the consumer with a useful or commercial choice.

According to a first aspect of the present invention, there is provided a refractive index sensor for analysing an analyte, the sensor comprising:

a strip waveguide for receiving an input light signal therein and transmitting the light signal, subject to manipulation as it propagates through the strip waveguide, to a detector for analysis with respect to the analyte; and a slot waveguide for sensing the analyte disposed thereon and for receiving a sensing signal, corresponding to said manipulation of the light signal, from the strip waveguide, wherein a grating is formed on a surface of the strip waveguide to enable coupling of the sensing signal from the strip waveguide to the slot waveguide, and the sensor is configured with enhanced sensitivity based on a sensitivity difference between the slot waveguide and the strip waveguide, and/or a group index difference between the slot waveguide and the strip waveguide.

Preferably, the sensor further comprises a substrate, wherein the strip waveguide and the slot waveguide are disposed on the substrate so as to be spaced apart and substantially parallel to each other.

Preferably, the sensing signal is in the form of a light signal, and the grating has a grating period configured to couple light signal at a particular resonant wavelength from the strip waveguide to the slot waveguide.

Preferably, the slot waveguide has a mode index which is subject to change based on the analyte disposed thereon, the change in the mode index results in a shift in the particular resonant wavelength of the light signal coupled from the strip waveguide to the slot waveguide, thereby enabling analysis of the analyte based on the shift in the particular resonant wavelength.

Preferably, the sensor is configured such that its sensitivity (S) is determined based on the following equation:

$$S = \lambda_0 \frac{\Delta S}{\Delta N_g}$$

where, $\lambda_0$ is the particular resonant wavelength of the light signal, $\Delta S$ is the sensitivity difference between the slot waveguide and the strip waveguide, and $\Delta N_g$ is the group index difference between the slot waveguide and the strip waveguide.

Preferably, the sensor is configured such that the sensitivity difference between the slot waveguide and the strip waveguide is increased and/or the group index difference between the slot waveguide and the strip waveguide is reduced.

Preferably, the strip waveguide is isolated to decrease its sensitivity so as to increase the sensitivity difference between the slot waveguide and the strip waveguide.

Preferably, the strip waveguide is enclosed by an isolation layer made of $SiO_2$ to isolate the strip waveguide from the analyte.

In another embodiment, the strip waveguide is enclosed by an isolation layer made of a polymer material to isolate the strip waveguide from the analyte.

Preferably, the polymer material has a thermal-optic coefficient selected for compensating a positive or negative temperature dependence of the sensor so as to reduce the temperature dependence of the sensor.

Preferably, the polymer material is made of WIR30-490 or SU-8.

Preferably, a width of the strip waveguide is configured to be about 600 nm to about 1000 nm.

Preferably, one or more parameters of the slot waveguide are configured to increase its sensitivity so as to increase the sensitivity difference between the slot waveguide and the strip waveguide, said one or more parameters include a width of the slot waveguide and/or a width of a gap of the slot waveguide.

Preferably, the slot waveguide is configured such that the width of the slot waveguide is increased and/or the width of the gap is reduced.

Preferably, the width of the slot waveguide is in the range of about 350 nm to about 550 nm, and the width of the gap is in the range of about 50 nm to about 300 nm.

Preferably, a plurality of gratings, spaced apart from each other, is formed on the surface of the strip waveguide, each grating having a different grating period configured for coupling a sensing signal at a respective resonance wavelength to the slot waveguide, thereby enabling wavelength multiplexed measurement.

Preferably, the slot waveguide and/or the strip waveguide are made of silicon nitride ($Si_3N_4$).

According to a second aspect of the present invention, there is provided a method of fabricating a refractive index sensor for analysing an analyte, the method comprising:

forming a strip waveguide for receiving an input light signal therein and transmitting the light signal, subject to manipulation as it propagates through the strip waveguide, to a detector for analysis with respect to the analyte; and forming a slot waveguide for sensing the analyte disposed thereon and for receiving a sensing signal, corresponding to said manipulation of the light signal, from the strip waveguide, wherein the method further comprises forming a grating on a surface of the strip waveguide to enable coupling of the sensing signal from the strip waveguide to the slot waveguide, and configuring the sensor with enhanced sensitivity based on a sensitivity difference between the slot waveguide and the strip waveguide, and/or a group index difference between the slot waveguide and the strip waveguide.

According to a third aspect of the present invention, there is provided a refractive index sensor device for analysing an analyte, the sensor device comprising:

a refractive index sensor comprising a strip waveguide and a slot waveguide;

a light source for outputting a light signal to the strip waveguide; and a detector for receiving the light signal from the strip waveguide for analysis with respect to the analyte;

wherein the strip waveguide is configured to receive the light signal therein from the light source and transmit the light signal, subject to manipulation as it propagates through the strip waveguide, to the detector for analysis, the slot waveguide is configured for sensing the analyte disposed thereon and for receiving a sensing signal, corresponding to said manipulation of the light signal, from the strip waveguide, a grating is formed on a surface of the strip waveguide to enable coupling of the sensing signal from the strip waveguide to the slot waveguide, and the refractive index sensor is configured with enhanced sensitivity based on a sensitivity difference between the slot waveguide and the strip waveguide, and/or a group index difference between the slot waveguide and the strip waveguide.

Preferably, the refractive index sensor device further comprises a polarization controller for receiving the light signal from the light source, and outputting a TE polarized light signal to the strip waveguide.

BRIEF DESCRIPTION OF THE DRAWINGS

Embodiments of the present invention will be better understood and readily apparent to one of ordinary skill in the art from the following written description, by way of example only, and in conjunction with the drawings, in which:

FIGS. 3A and 3B depict the field distributions for the strip waveguide and slot waveguide, respectively, of the sensor having exemplary parameters.

FIG. 3C depicts a graph showing the dependences of the mode index $N_{eff}$ of the two waveguides and the mode index difference $\Delta N_{eff}$ between the two waveguides 104, 112 as a function of the wavelength 2;

FIG. 3D depicts a graph showing the dependences of the mode index $N_{eff}$ of the two waveguides and the mode index difference $\Delta N_{eff}$ between the two waveguides 104, 112 as a function of the external refractive index $n_{ex}$;

DETAILED DESCRIPTION

Embodiments of the present invention seek to provide a highly sensitive reflective index (RI) sensor for analyzing an analyte, and a method of fabricating the reflective index sensor. Details of the RI sensor according to exemplary embodiments of the present invention will now be described.

Figure 1A:
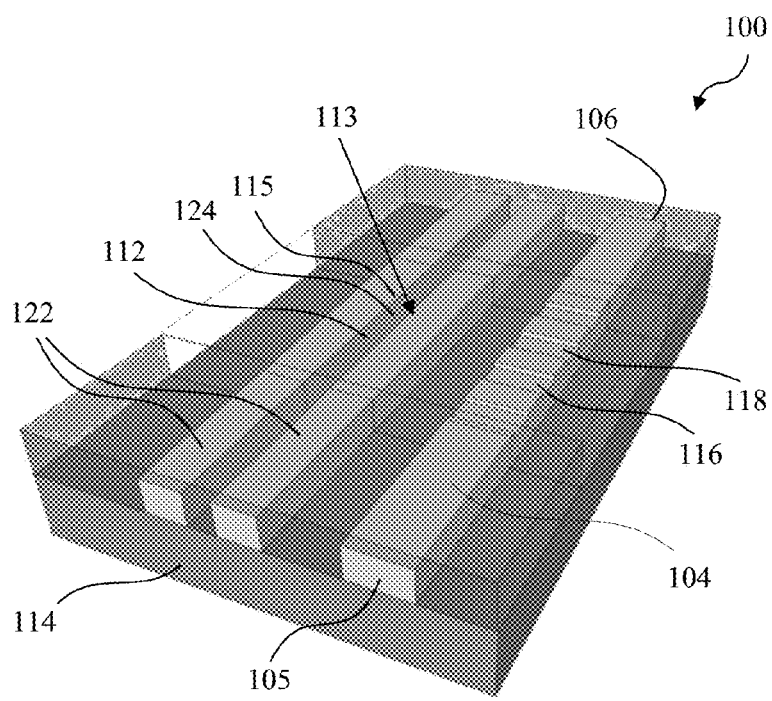
FIG. 1A depicts a schematic perspective view of the RI sensor according to an exemplary embodiment of the present invention.
Figure 1B:
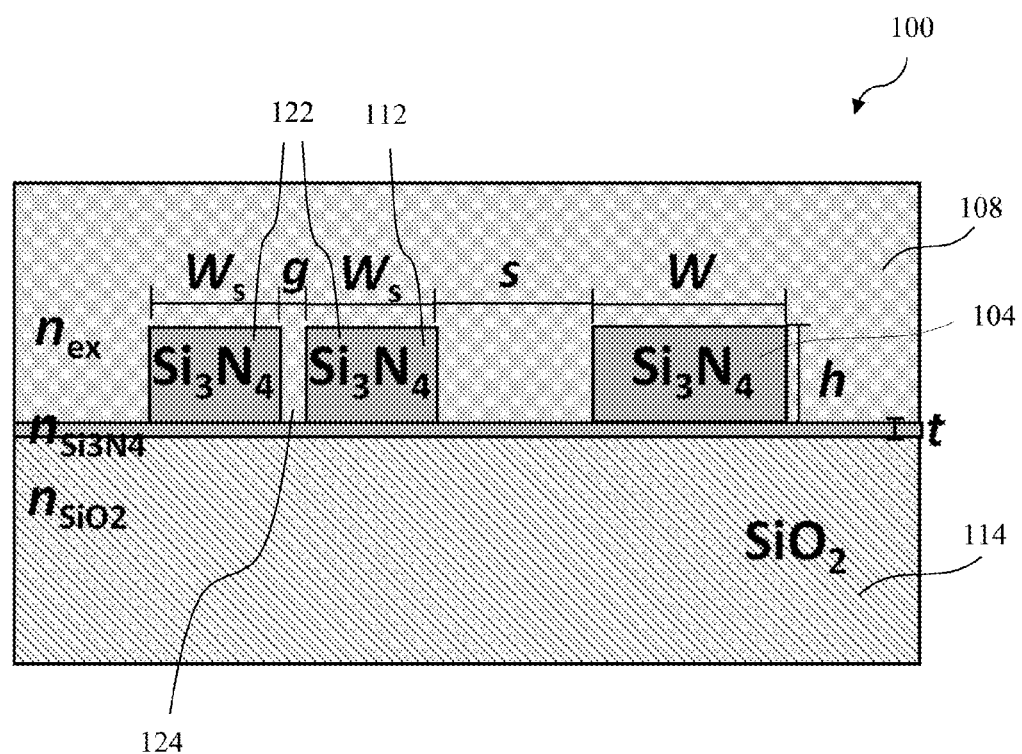
FIG. 1B depicts a schematic cross-sectional view of the RI sensor.
Figure 10:
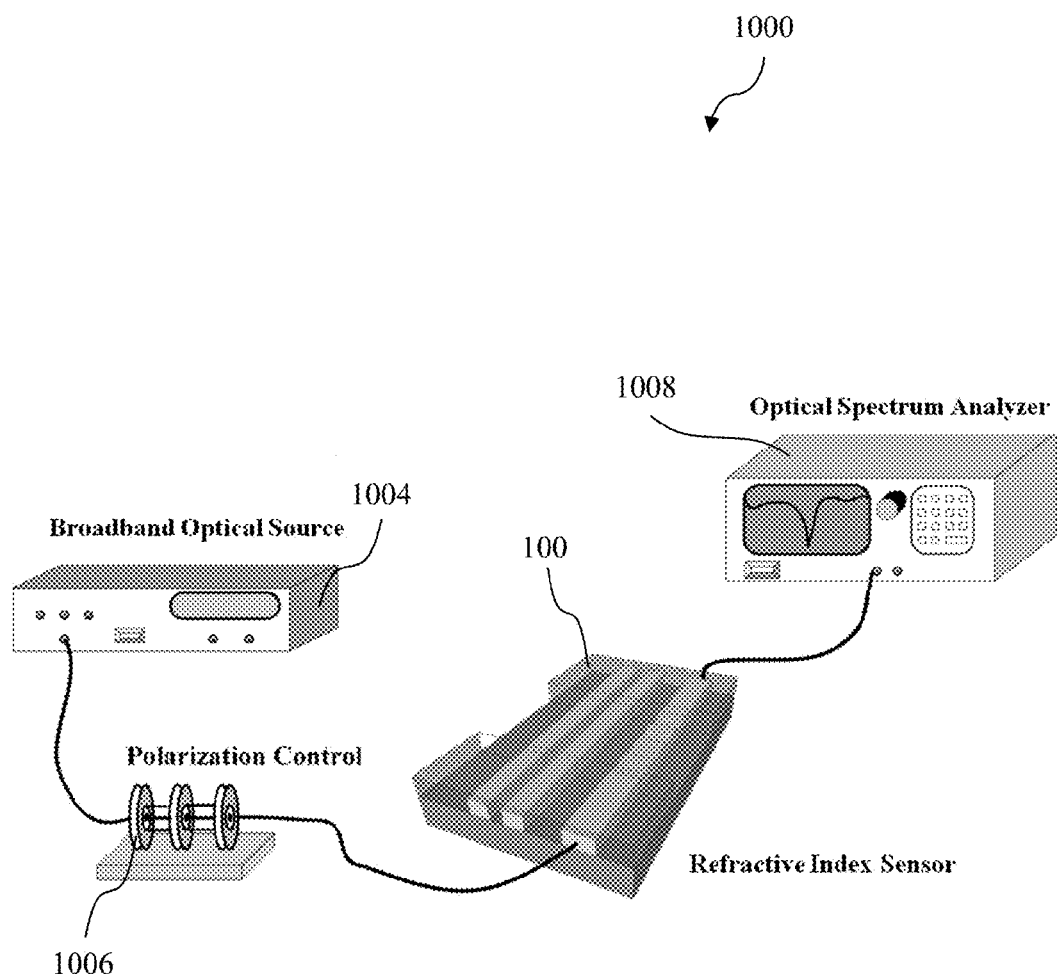
FIG. 10 depicts a refractive index sensor device for analysing an analyst according to an embodiment of the present invention.

FIG. 1A depicts a schematic perspective view and FIG. 1B depicts a schematic cross-sectional view of the RI sensor 100 according to an exemplary embodiment of the present invention. As illustrated, the sensor 100 for analysing an analyte, such as in biochemical analysis, includes a strip waveguide 104 for receiving an input light signal therein and transmitting the light signal, subject to manipulation as it propagates through the strip waveguide 104, to a detector for analysis with respect to the analyte 108. For example, the input light signal may be a broad-band light from a broad-band optical light source 1004 and the detector may be an optical spectrum analyser (OSA) 1008 as shown in FIG. 10. The input light signal is received at one end (e.g., an input end) 105 from the light source 1004 and output at another end (e.g., an output end) 106 of the strip waveguide 104. The sensor 100 further includes a slot waveguide 112 for sensing the analyte 108 disposed thereon and for receiving a sensing signal, corresponding to the above-mentioned manipulation of the light signal, from the strip waveguide 104. With this configuration, the slot waveguide 112 functions as a sensing waveguide while the strip waveguide 104 functions as a signal waveguide for the optical signal.

In practice, the analyte 108 may be disposed in a sensing area 113 generally indicated by the dashed enclosure in FIG. 1A, and preferably on a section 115 of the slot waveguide 112 opposing a grating section 116 (described below) of the strip waveguide 104. In the exemplary embodiment of FIGS. 1A and 1B, the analyte 108 is shown in FIG. 1B to be disposed on or covers both the strip waveguide 104 and the slot waveguide 112 in the sensing area 113. However, it is neither necessary nor essential for the analyte to be disposed on the strip waveguide 104 since it is the slot waveguide 112 that functions as the sensing waveguide.

The sensor 100 preferably further includes a substrate 114, and the strip waveguide 104 and the slot waveguide 112 are disposed on the substrate 114 so as to be side by side. More specifically, the strip waveguide 104 and the slot waveguide 112 are spaced apart by a distance s (see FIG. 1B) and substantially parallel to each other.

Figure 2:
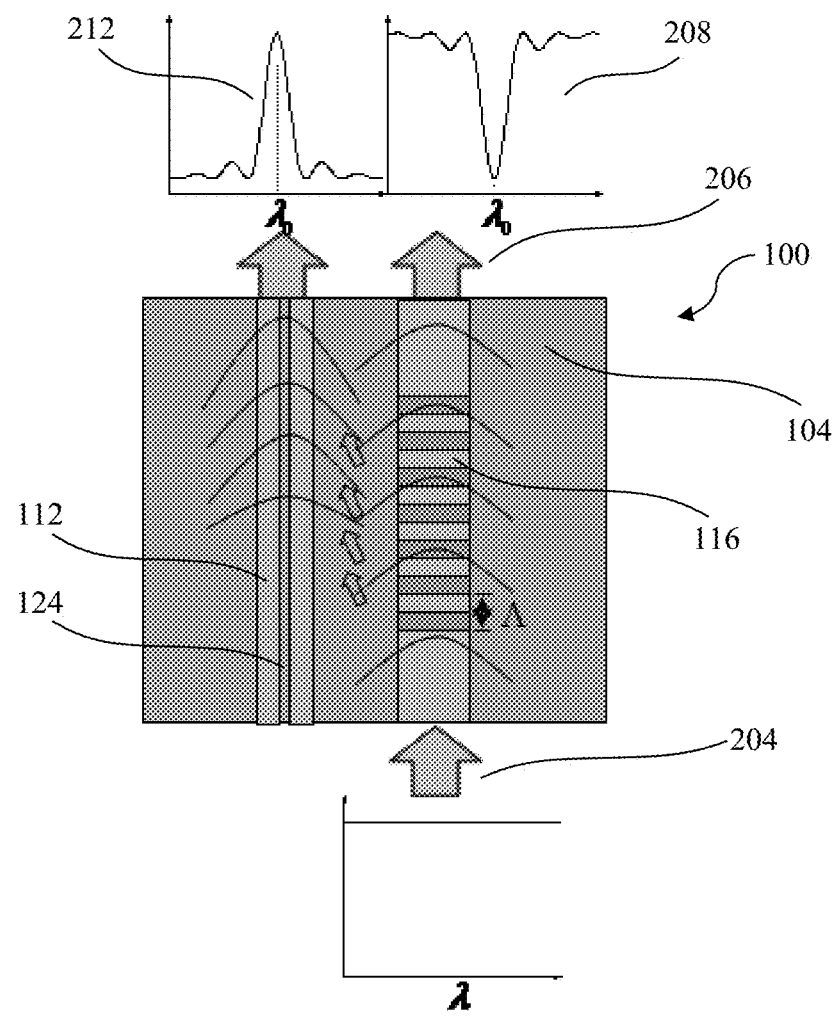
FIG. 2 illustrates the coupling of the sensing signal from the strip waveguide to the slot waveguide and shows the transmission spectra at the outputs of the two waveguides.

In the exemplary embodiment, a grating 116 is formed on a surface 118 of the strip waveguide 104 to enable coupling of the sensing signal from the strip waveguide 104 to the slot waveguide 112. This coupling of the sensing signal is schematically illustrated in FIG. 2. The sensing signal is in the form of a light signal, and the grating 116 has a grating period Λ configured to couple light signal at a particular resonant wavelength $\lambda_0$ from the strip waveguide 104 to the slot waveguide 112. Furthermore, the sensor 100 is configured with enhanced sensitivity based on a sensitivity difference ΔS between the slot waveguide 112 and the strip waveguide 104, and/or a group index difference $\Delta N_g$ between the slot waveguide 112 and the strip waveguide 104. This will be described in further detail later below.

The slot waveguide 112 comprises two parallel strips (or rails) 122 having a high refractive index separated by a low-index region (i.e., slot or gap) 124. As shown in FIG. 1B, the strip waveguide 104 has a width W, the slot waveguide 112 has a width $W_s$, and the gap 124 has a width g. The strip waveguide 104 and the slot waveguide 112 may have the same height h and rib height t. For clarity and illustration purpose, exemplary embodiments are hereinafter described with the strip waveguide 104 and slot waveguide 112 made of silicon nitride ($Si_3N_4$), and the substrate 114 made of $SiO_2$. It will be appreciated to a person skilled in the art that the waveguides 104, 112 and the substrate 114 are not limited to such materials and other suitable/appropriate materials are within the scope of the present invention. For example, the strip waveguide 104 and the slot waveguide 112 may instead be made of Silicon (Si) or high refractive index polymers. If different materials are used, it will be appreciated to a person skilled in the art that the above-mentioned design parameters of the sensor (e.g., g, W, $W_s$, s, etc.) 100 may also have to be adjusted accordingly. In FIG. 1B, the refractive index of $Si_3N_4$, $SiO_2$, and the external medium (analyte) 108 are denoted as $n_{Si3N4}$, $n_{SiO2}$ and $n_{ex}$, respectively.

As shown in FIG. 1A, the grating 116 is formed on a top surface 118 of the strip waveguide 104. Without the grating 116, no light coupling would occur between the strip waveguide 104 and the slot waveguide 112 since they are not synchronous in phase (i.e. they have different propagation constants). In the exemplary embodiment, the phase synchronism is achieved with the grating 116 formed on the top surface 118 of the strip waveguide 104. In this regard, with a predetermined grating period Λ, a light power transfer from the strip waveguide 104 to the slot waveguide 112 is obtained at a particular wavelength (resonance wavelength $\lambda_0$) satisfying the phase-matching condition:

$$\lambda_0 = (N_{eff}^{strip} - N_{eff}^{slot})\Lambda = \Delta N_{eff}\Lambda, \quad (1)$$

where $N_{eff}^{strip}$ and $N_{eff}^{slot}$ are the mode indices of the strip waveguide 104 and slot waveguide 112, respectively. Therefore, according to Equation (1), the grating coupler 116 is wavelength-selective. As illustrated in FIG. 2, when a broad-band light 204 is launched into the strip waveguide 104, light at the resonance wavelength $\lambda_0$ is coupled to the slot waveguide 112. This produces a band-rejection spectrum 208 (center wavelength at $\lambda_0$) in the launching strip waveguide 104 while a band-pass spectrum 212 (center wavelength at $\lambda_0$) in the neighbouring slot waveguide 112. FIG. 2 shows the transmission spectra 208, 212 at the outputs of the two waveguides 104, 112 as a result of the grating coupler 116 having a predetermined grating period Λ. This illustrates the manipulation of the input light signal 204 as it propagates through the strip waveguide 104, and the sensing signal coupled to the slot waveguide 112 corresponding to such a manipulation of the input light signal 204.

As shown in FIGS. 1A and 1B, the slot waveguide 112 functions as a sensing waveguide while the strip waveguide 104 functions as a signal waveguide for the optical signal guiding and detection. As the refractive index of the analyte ($n_{ex}$) 108 changes, the mode indices of the slot waveguide 112 and strip waveguide 104 change accordingly. This therefore results in a change in the difference $\Delta N_{eff}$ between the mode indices of the strip waveguide 104 ($N_{eff}^{strip}$) and the slot waveguide 112 ($N_{eff}^{slot}$), which in turn leads to a shift in the resonance wavelength $\lambda_0$ of the light coupled from the strip waveguide 104 to the slot waveguide 112. The resonance wavelength $\lambda_0$ of the light signal 206 output from the strip waveguide 104 will therefore shift correspondingly and can be detected by the detector 1008. Accordingly, the analyte 108 may be analysed based on this shift in the resonant wavelength $\lambda_0$. Accordingly, the sensitivity S of the sensor 100 may be defined as the degree of such a shift in the resonant wavelength $\lambda_0$ in response to the analyte 108.

With the configuration of the sensor 100 as described in the example embodiment, the RI sensitivity S of the sensor 100 may be defined as:

$$S = \frac{d\lambda_0}{dn_{ex}} = \frac{\lambda_0}{(N_g^{strip} - N_g^{slot})}\left(\frac{\partial N_{eff}^{strip}}{\partial n_{ex}} - \frac{\partial N_{eff}^{slot}}{\partial n_{ex}}\right) = \lambda_0 \frac{\Delta S}{\Delta N_g} \quad (2)$$

where

-continued $$N_g^{strip} = N_{eff}^{strip} - \lambda \frac{dN_{eff}^{strip}}{d\lambda},$$ (3)

$$N_g^{slot} = N_{eff}^{slot} - \lambda \frac{dN_{eff}^{slot}}{d\lambda},$$

$$\Delta N_g = N_g^{strip} - N_g^{slot},$$

$$S^{strip} = \frac{\partial N_{eff}^{strip}}{\partial n_{ex}},$$ (4)

$$S^{slot} = \frac{\partial N_{eff}^{slot}}{\partial n_{ex}},$$

$$\Delta S = S^{strip} - S^{slot}.$$

According to Equations (2) to (4), it is found that the sensitivity S of the sensor 100 described in the example embodiment is proportional to the sensitivity difference ΔS between the strip waveguide 104 and the slot waveguide 112. With this configuration, due to the high intensity field distribution in the slot region 124 of the slot waveguide 112, the sensitivity $S^{slot}$ of the slot waveguide 112 is much larger than that $S^{strip}$ of the strip waveguide 104, therefore resulting in a larger sensitivity difference ΔS. In addition, as can be seen from Equation (2), the sensitivity S of the sensor 100 is also inversely proportional to the group index difference $\Delta N_g$ between the strip waveguide 104 and the slot waveguide 112. The group index difference $\Delta N_g$ according to the example embodiment is configured to have a small value. Accordingly, the sensor 100 can be configured with greatly enhanced sensitivity based on the above factors (i.e., the sensitivity difference ΔS and/or the group index difference $\Delta N_g$). In contrast, the sensitivity of conventional single slot or strip waveguide based sensors is typically only inversely proportional to the group index $N_g$ (i.e., not the group index difference) which generally has a much larger value (e.g., about 2 to 4). Therefore, such conventional sensors have a much smaller sensitivity.

For illustrate purpose only and without limitation, a sensor 100 according to the exemplary embodiment having the following exemplary parameters will now be examined, including an exemplary calculation of the sensitivity S of the sensor 100. In particular, the exemplary parameters are: $n_{Si3N4}$=2.0, $n_{ex}$=1.333, $n_{SiO2}$=1.444, h=400 nm, g=200 nm, s=1 μm, W=1 μm, $W_s$=450 nm, and t=0 nm. In this example, only the TE polarization is considered.

FIGS. 3A and 3B show the field distributions for the strip waveguide 104 and slot waveguide 112, respectively, of the sensor 100 with the above-mentioned exemplary parameters. It can be observed from FIG. 3B that the light intensity inside the nanoscale (200 nm) low refractive index slot region 124 of the slot waveguide 112 is very strong. FIGS. 3C and 3D illustrate the graphs showing the dependences of the mode index $N_{eff}$ of the two waveguides 104, 112 and the mode index difference $\Delta N_{eff}$ between the two waveguides 104, 112 as a function of the wavelength 2 (i.e., FIG. 3C) and external refractive index $n_{ex}$ (i.e., FIG. 3D). Therefore, the group index $N_g^{strip}$, $N_g^{slot}$ and the sensitivity $S^{strip}$, $S^{slot}$ of each waveguide 104, 112 may be calculated from the graphs shown in FIGS. 3C and 3D. The characteristics/properties of the sensor 100 calculated, including the sensitivity S of the sensor 100, are shown in Table 1 below.

TABLE 1

Properties of the exemplary sensor shown in FIG. 1A (having the above-mentioned exemplary parameters)

| $N_g^{strip}$ | $N_g^{slot}$ | $\Delta N_g$ | $S_{strip}$ | $S_{slot}$ | ΔS | Sensitivity (S) $d\lambda_0/dn_{ex}$ (nm/RIU) |
|---|---|---|---|---|---|---|
| 2.0479 | 1.7902 | 0.2577 | 0.1793 | 0.4222 | −0.2429 | −1461.0 |

As shown in Table 1, the sensitivity S of the sensor 100 in this example can advantageously be as large as −1461 nm/RIU. It will be understood that the negative sign implies that the resonance wavelength $\lambda_0$ decreases as the external refractive index increases ($n_{ex}$). Significantly, this sensitivity S value is about 20 times larger than that of a conventional strip waveguide ring resonator sensor and about 7 times larger than a conventional slot waveguide ring resonator sensor.

Therefore, the configuration of the sensor 100 as described in the exemplary embodiment (i.e., based on the sensitivity difference ΔS between the slot waveguide and the strip waveguide, and/or the group index difference $\Delta N_g$ between the slot waveguide 112 and the strip waveguide 104) has been demonstrated to advantageously result in a highly sensitive refractive index sensor 100.

According to further embodiments of the present invention, the sensitivity (S) of the sensor 100 can be further enhanced by configuring/adjusting the sensitivity difference ΔS between the slot waveguide 112 and the strip waveguide 104, and/or the group index difference $\Delta N_g$ between the slot waveguide 112 and the strip waveguide 104. This is evident from Equation (2) described above which shows that $$S = \lambda_0 \frac{\Delta S}{\Delta N_g}.$$

Therefore, by configuring the sensor 100 such that the sensitivity difference ΔS between the slot waveguide 112 and the strip waveguide 104 is increased and/or the group index difference $\Delta N_g$ between the slot waveguide 112 and the strip waveguide 104 is reduced, the sensitivity S of the sensor 100 may be further enhanced.

Figure 4:
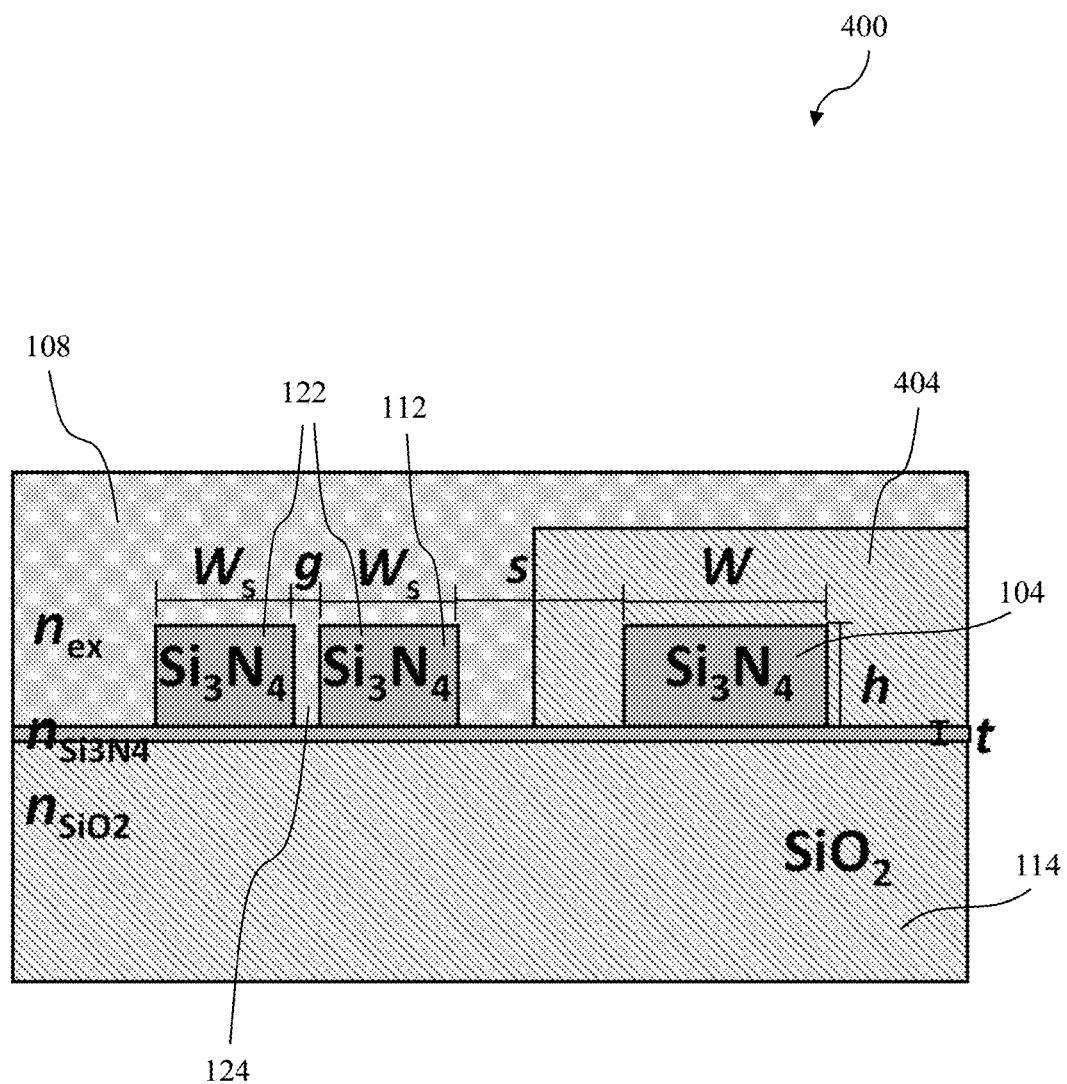
FIG. 4 depicts a schematic cross-sectional view of a sensor according to another embodiment of the present invention whereby the strip waveguide is isolated.

In exemplary embodiments, to increase the sensitivity difference ΔS between the slot waveguide 112 and the strip waveguide 104, the sensitivity $S^{strip}$ of the strip waveguide 104 is decreased and/or the sensitivity $S^{slot}$ of the slot waveguide 112 is increased. In a preferred embodiment, the sensitivity $S^{strip}$ of the strip waveguide 104 is decreased by isolating the strip waveguide 104 as illustrated in FIG. 4. The sensor 400 depicted in FIG. 4 is the same as the sensor 100 depicted in FIG. 1B, except that the strip waveguide 104 of the sensor 400 is enclosed by an insolation layer 404 to isolate it from the external analyte 108. It should be noted that the same or similar reference numerals in FIGS. 1A and 1B are applied to the same or similar parts/components throughout the drawings (including FIG. 4), and the description of the same or similar parts/components will be omitted or simplified. A preferred or suitable material for the isolation layer 404 is silicon dioxide ($SiO_2$). It will be appreciated to a person skilled in the art that the isolation layer 404 is not limited to an $SiO_2$ isolation layer and other suitable/appropriate materials are within the scope of the present invention. For example, in a preferred embodiment described with reference to FIG. 8A later below, the isolation layer is made of a low index material such as a polymer material (e.g., an epoxy resin such as SU-8 and various types of photoresist).

For illustrate purpose only and without limitation, the characteristics/properties of the sensor 400 having the same exemplary parameters as described hereinbefore and with the SiO$_2$ isolation layer depicted in FIG. 4 are calculated and shown in Table 2 below.

TABLE 2

Properties of the exemplary sensor shown in FIG. 4 (having the above-mentioned exemplary parameters).

| $N_g^{strip}$ | $N_g^{slot}$ | $\Delta N_g$ | $S_{strip}$ | $S_{slot}$ | $\Delta S$ | Sensitivity (S) $d\lambda_0/dn_{ex}$ (nm/RIU) |
|---|---|---|---|---|---|---|
| 2.0248 | 1.7858 | 0.2390 | 0.0026 | 0.4193 | −0.4167 | −2702.4 |

By comparing the sensitivity $S_{strip}$ of the strip waveguide 104 in Tables 1 and 2, it can be clearly seen that $S_{strip}$ is significantly reduced after the SiO$_2$ isolation. As a result, the sensitivity difference $\Delta S$ between the slot waveguide 112 and the strip waveguide 104 increased significantly, which therefore leads to a correspondingly large increase in the sensitivity of the sensor 400. As shown in Table 2, the sensitivity of the sensor 400 calculated is about −2702.4 nm/RIU which is almost 2 times larger than that the sensor 100 described hereinbefore without the strip waveguide being isolated. This demonstrates an effective way to decrease the sensitivity of the strip waveguide 104 in the interest of increasing the sensitivity of the sensor 400.

Figure 5A:
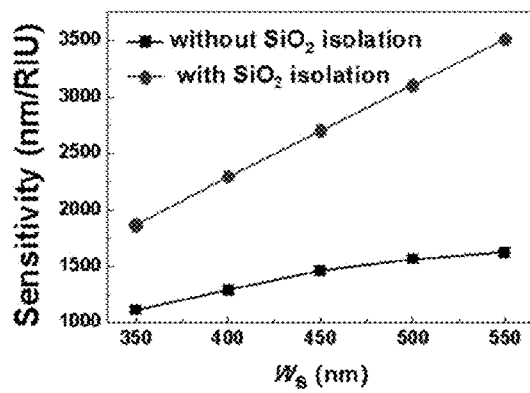
FIGS. 5A to 5C show the sensitivity of the two sensors (i.e., with and without isolation) against the width $W_s$ of the slot waveguide, the width g of the gap 124 of the slot waveguide, and the rib height t.
Figure 5B:
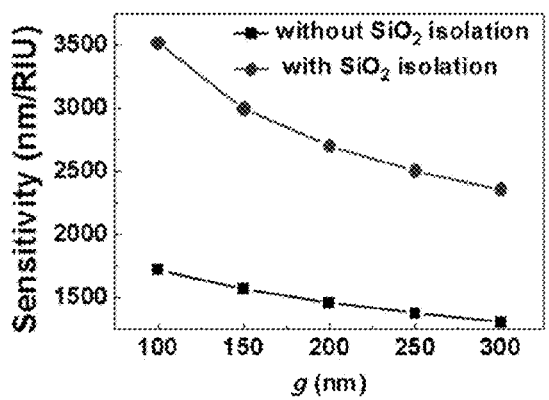
Figure 5C:
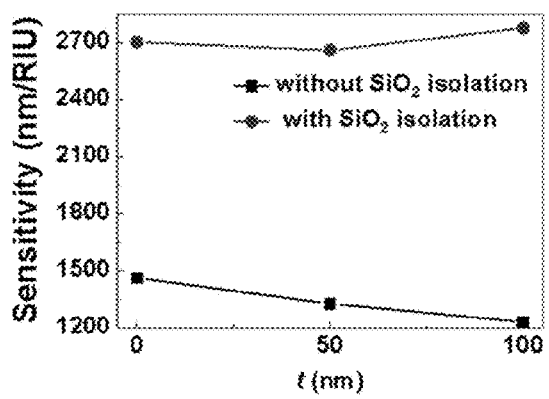

As mentioned above, the sensitivity difference $\Delta S$ between the slot waveguide 112 and the strip waveguide 104 can also be increased by increasing the sensitivity $S^{slot}$ of the slot waveguide 112. In an embodiment, this can be achieved by configuring one or more parameters of the slot waveguide 112. To demonstrate this, FIGS. 5A, 5B, and 5C show the sensitivity S of the sensors 100, 400 against the width $W_s$ (in the range of about 350 nm to 550 nm) of the slot waveguide 112, the width g (in the range of about 100 nm to 300 nm) of the gap 124 of the slot waveguide 112, and the rib height t (in the range of 0 to 100 nm). From FIGS. 5A and 5B, for both sensors 100, 400, it can be clearly seen that the sensitivity S increases as the width $W_s$ of the slot waveguide 112 and/or the width g of the gap 124 of the slot waveguide 112 decreases. Therefore, it has been demonstrated that by configuring/adjusting the parameters of the slot waveguide 112, the sensitivity S of the sensors 100, 400 can be as high as about 1700 nm/RIU and 3500 nm/RIU, respectively. On the other hand, from FIG. 5C, the sensitivity S of the sensors 100, 400 has only be found to weakly depend on the rib height t.

In a preferred embodiment, the width $W_s$ of the slot waveguide 112 is in the range of about 350 nm to 550 nm, and more preferably 450 nm to 550 nm, the width g of the gap 124 of the slot waveguide 112 is in the range of about 100 nm to 300 nm, and more preferably 100 nm to 200 nm, and the rib height t is in the range of about 0 nm to 100 nm.

The coupling coefficient and the transmission spectrum of the grating 116 will now be described. The transmission spectrum at the output of the strip waveguide 104 can be obtained based on the following equation:

$$T(\lambda) = 1 - \frac{\kappa^2}{\kappa^2 + \delta^2/4} \sin^2 \sqrt{\kappa^2 + \delta^2/4} \, L \quad (5)$$

where $$\delta = \frac{2\pi}{\lambda} \Delta N_{eff} - \frac{2\pi}{\Lambda} \quad (6)$$

In the above equations, L is the grating length and κ is the coupling coefficient used to characterize the strength of the grating and is obtained with:

$$\kappa = \frac{2(n_{Si_3N_4}^2 - n_{ex}^2)}{\lambda c \mu_0} \int\int_A \vec{e}_{strip} \cdot \vec{e}_{slot}^* dA, \quad (7)$$

where c and $\mu_0$ are the speed of light in free space and the vacuum permeability. $\vec{e}_{strip}$ and $\vec{e}_{slot}$ are the normalized fields of strip waveguide 104 and slot waveguide 112, respectively. A denotes the grating area. According to Equation (5), when κL=π/2 and δ=0, 100% coupling occurs at the resonance wavelength $\lambda_0$.

Figure 6:
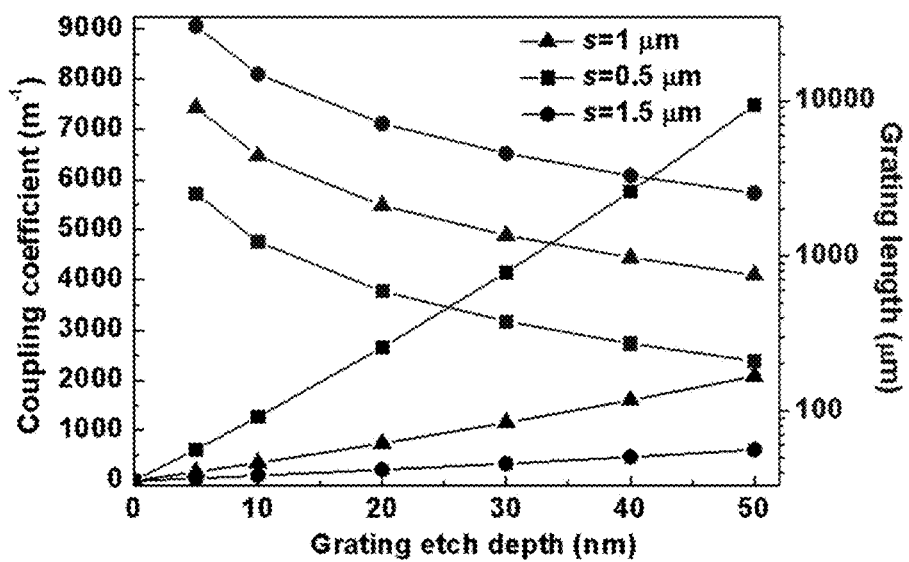
FIG. 6 depicts the variation of the coupling coefficient and corresponding grating lengths required for achieving $\kappa L = \pi/2$ as a function of the etch depth for three exemplary values of separation distance s.

According to an embodiment, the grating strength (i.e., coupling coefficient) can be controlled by configuring the grating etch depth on the top surface 118 of the strip waveguide 104. To demonstrate this, FIG. 6 shows the variation of the coupling coefficient as a function of the etch depth for three values of separation distance s. It can be observed that the coupling coefficient increases as the etch depth increases. In addition, smaller separation distance results in larger coupling coefficient at the same etch depth. The corresponding grating lengths required for achieving κL=π/2 are also shown in FIG. 6. For example, with L=1500 μm, the coupling coefficient required for achieving a maximum contrast is given by κ=π/2 L=1.047×10³ m⁻¹, which according to FIG. 6, requires an etch depth of about 28 nm (about 7% of the thickness of the waveguide height).

Figure 7A:
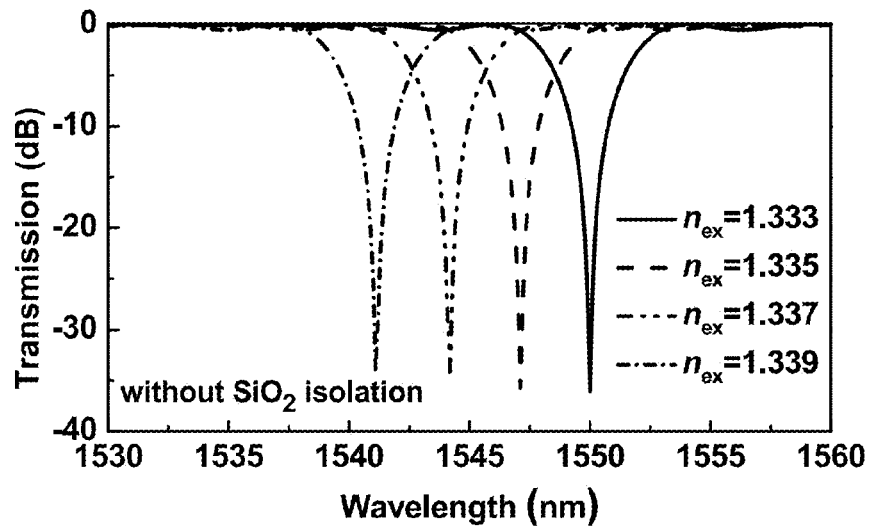
FIGS. 7A and 7B show the transmission spectra for the two sensors (i.e., without and with isolation), respectively, at different values of external refractive index $n_{ex}$.
Figure 7B:
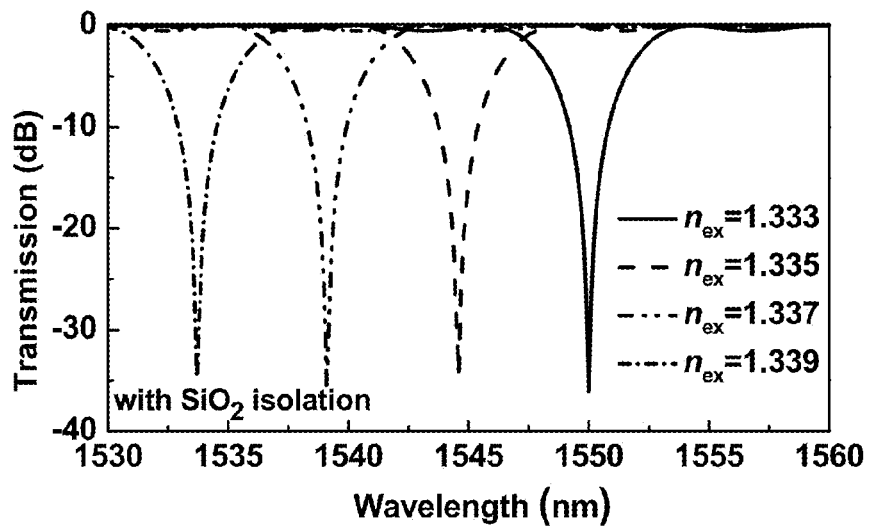
Figure 7C:
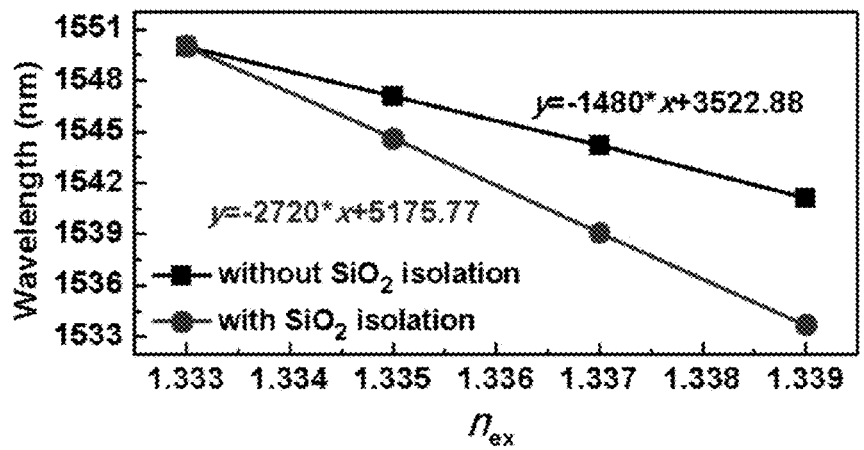
FIG. 7C illustrates the linear dependence of the resonance wavelength $\lambda_0$ on the external refractive index $n_{ex}$.

FIGS. 7A and 7B show the transmission spectra for the two sensors 100, 400 (i.e., without and with SiO$_2$ isolation), respectively, at different values of external refractive index $n_{ex}$. The grating lengths for both sensors 100, 400 are set to 2000 μm. In both Figures, the resonance wavelength $\lambda_0$ shifted to shorter wavelength as the external refractive index increases. By comparing FIGS. 7A and 7B, it can be observed that the sensor 400 with SiO$_2$ isolation is more sensitive than the sensor 100 without SiO$_2$ isolation. In FIG. 7C, the dependence of the resonance wavelength $\lambda_0$ on the external refractive index $n_{ex}$ are shown to be linear.

Figure 8A:
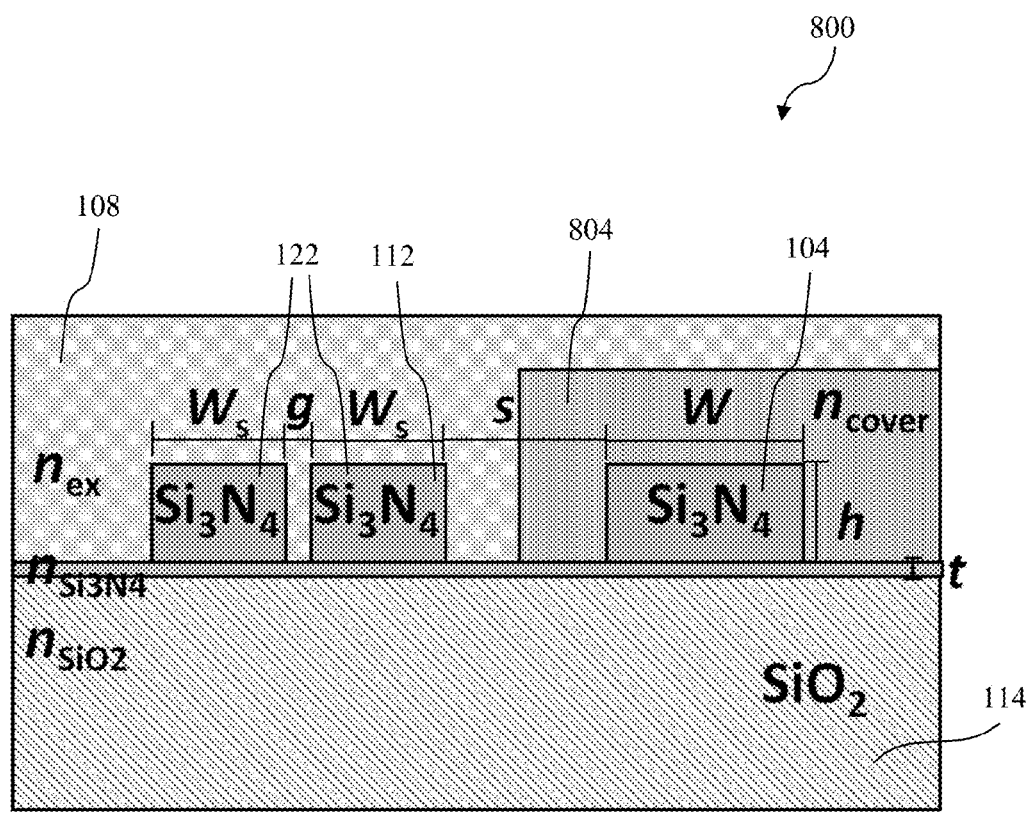
FIG. 8A depicts a schematic cross-sectional view of a sensor according to yet another embodiment of the present invention for reducing temperature dependence of the sensor.

In a further embodiment, a sensor 800 as depicted in FIG. 8A is configured with reduced or minimal temperature dependence. The sensor 800 depicted in FIG. 8A is the same as the sensor 100 depicted in FIG. 1B or the sensor 400 depicted in FIG. 4 except that the strip waveguide 104 of the sensor 400 is isolated or enclosed by a polymer layer 804. It should be noted that the same or similar reference numerals are applied to the same or similar parts/components throughout the drawings, and the description of the same or similar parts/components will be omitted or simplified.

In the embodiment, the temperature dependence of the resonance wavelength $\lambda_0$ is calculated as follow:

$$\frac{d\lambda_0}{dT} = \frac{\lambda_0}{\Delta N_g} \left( \frac{\partial \Delta N_{eff}}{\partial n_{SiO_2}} C_{SiO_2} + \frac{\partial \Delta N_{eff}}{\partial n_{ex}} C_{ex} + \right. \quad (8)$$

$$\left. \frac{\partial \Delta N_{\text{eff}}}{\partial n_{\text{cover}}} C_{\text{cover}} + \frac{\partial \Delta N_{\text{eff}}}{\partial n_{Si_3N_4}} C_{Si_3N_4} \right) = \frac{\lambda_0}{\Delta N_g} F_t,$$

where $C_{SiO2}$, $C_{ex}$, $C_{cover}$, $C_{Si3N4}$ are thermal-optic coefficients (TOC) for the $SiO_2$ substrate 114, external analyte 108, polymer cover layer 804 for isolation, and $Si_3N_4$, respectively. In this example, it was found that the sensor 400 has a positive temperature dependence (i.e., resonance wavelength $\lambda_0$ shifts to longer wavelength as temperature increases). To address this positive temperature dependence, the embodiment provides a polymer cover 804 with a negative TOC as an isolation layer instead of the $SiO_2$ layer 404 as disclosed in the embodiment of FIG. 4 to compensate for the temperature dependence of the sensor 400. It was found that $F_t$ in Eq. (8) can be a small value close to zero when a polymer material with an appropriate negative TOC is used. That is, selecting a polymer material having a TOC which can substantially compensate the positive temperature dependence of the sensor such that the net temperature dependence is minimal or substantially reduced, and vice versa. Therefore, the temperature dependence of the sensor 800 can advantageously be significantly reduced or substantially eliminated.

Figure 8B:
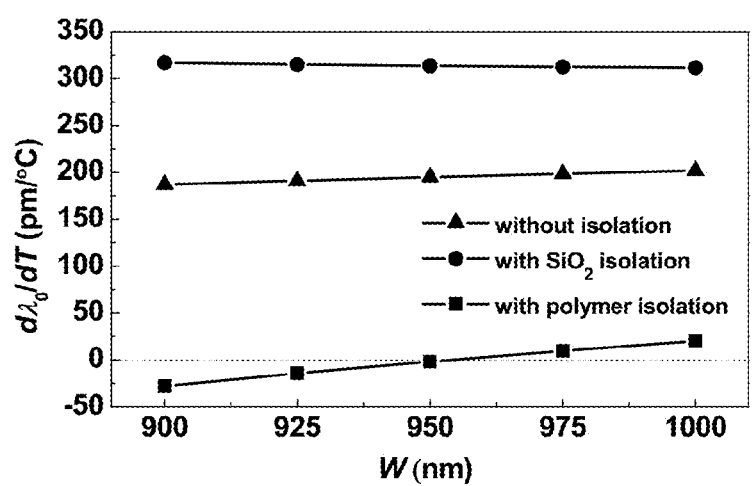
FIG. 8B shows the temperature dependence of the resonance wavelength for the sensors of FIGS. 1B, 4 and 8 at different values of strip waveguide width.

For illustration purpose, an experiment was conducted for each of the sensors 100, 400, 800 with the following parameters: $C_{SiO2}=1.0\times10^{-5}/^\circ$ C., $C_{ex}=-8.0\times10^{-5}/^\circ$ C. (i.e., for water), $C_{cover}=-1.8\times10^{-4}/^\circ$ C., $C_{Si3N4}=4.0\times10^{-5}/^\circ$ C., $n_{cover}=1.49$ (the TOC and the refractive index are typical values of polymers). FIG. 8B shows the temperature dependence of the resonance wavelength for each of the three sensors 100, 400, 800 at different values of strip waveguide width (from 900 nm to 1000 nm). It can be seen that the sensors without and with $SiO_2$ isolation (i.e., 100, 400) have a positive temperature dependence of about 200 pm/° C. and about 310 pm/° C., respectively. On the other hand, when a polymer isolation layer 804 is used, the temperature dependence is significantly reduced to be less than 20 pm/° C. for a large range of strip waveguide width (i.e., large tolerance). In addition, the temperature dependence can be further reduced to substantially zero by choosing a strip waveguide 104 having a width of about 950 nm. This can be derived from FIG. 8B since the crossing point of the dashed line (corresponding to zero temperature sensitivity) and the curve with polymer isolation is located when W is around 950 nm. Therefore by applying a polymer isolation layer 804, not only is the sensitivity enhanced, but the temperature dependence is also greatly reduced. In general, any polymer material that has an appropriate TOC is suitable, and preferably the polymer material is patternable. For example and without limitation, the polymer material may be WIR30-490 or SU-8.

Figure 9:
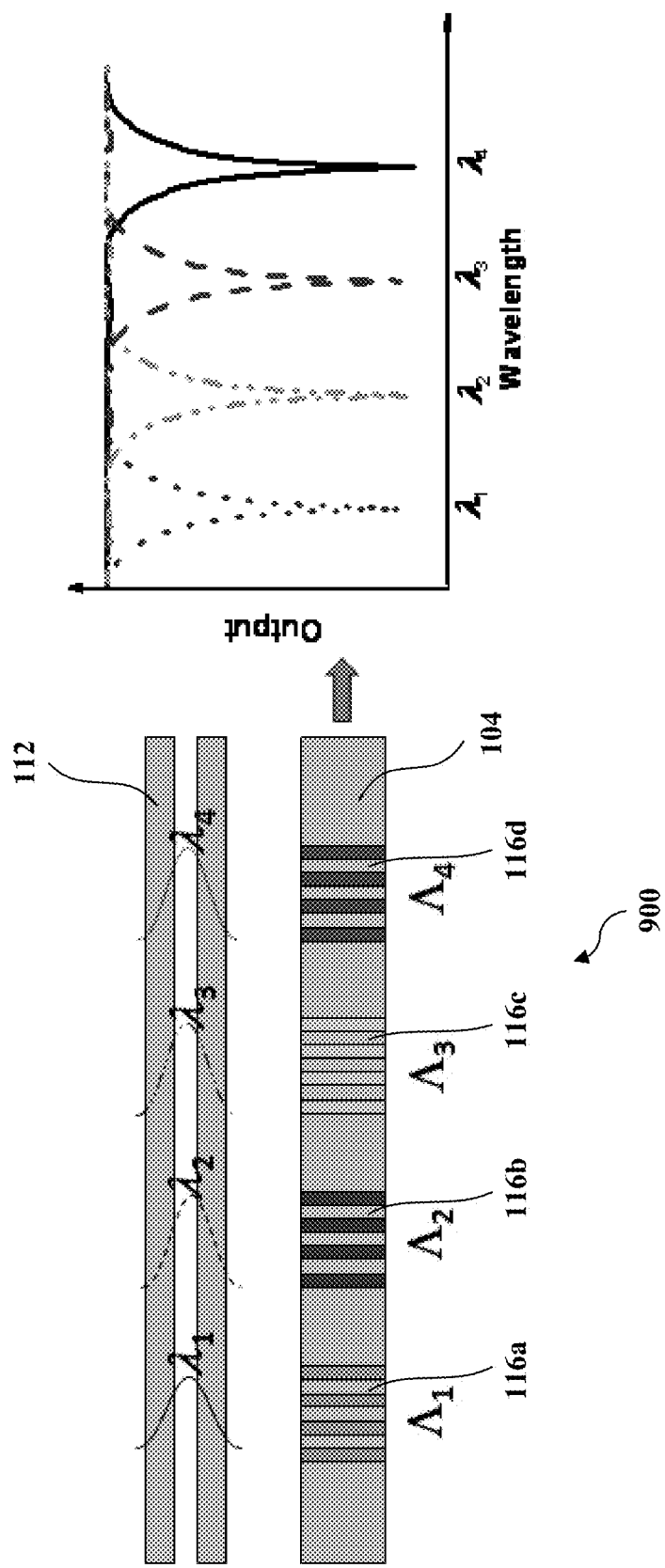
FIG. 9 depicts a sensor according to an embodiment of the present invention configured for enabling wavelength multiplexed measurement.

According to another embodiment, the sensor 900 is configured so as to enable wavelength multiplexed measurement. As mentioned hereinbefore, the grating 116 is intrinsically wavelength-selective. Therefore, the sensor 100, 400, 800 can be extended to a configuration suitable for wavelength multiplexed measurement. FIG. 9 illustrates a top schematic view of a sensor 900 capable of wavelength multiplexed sensing where four cascaded gratings 116a, 116b, 116c, and 116d with different periods $\Lambda_1, \Lambda_2, \Lambda_3$, and $\Lambda_4$ (corresponding to different resonance wavelengths) are formed along the top surface 118 of the strip waveguide 104. Each grating 116 generates a sensing signal at the respective resonance wavelength $\lambda_1, \lambda_2, \lambda_3$, and $\lambda_4$, therefore, a spectrum with four peaks can be observed at the output of the strip waveguide 104. The wavelength of each peak can then be monitored or detected for wavelength multiplexed measurement.

Accordingly, embodiments of the present invention provide a highly sensitive refractive index sensor, such as in biochemical analysis, based on grating assisted co-directional light coupling between a strip waveguide 104 and a slot waveguide 112. The sensor has a high sensitivity and can be further enhanced by isolating the strip waveguide 104 and/or optimizing the slot waveguide parameters. With a polymer isolation layer, the sensor can further achieve minimal or significantly reduced temperature dependence. In addition, the sensor can be configured to have wavelength multiplexed measurement capability due to the intrinsic wavelength-selective property of the gratings. The sensors disclosed in the exemplary embodiments have a wide range of applications such as but not limited to clinical applications where multiplexed detection of biomolecules with low detection limit is desirable. For example, other applications can be in the fields of environmental monitoring, and food safety and drug screening, such as a gas sensor for low-concentration explosive gas detection.

FIG. 10 depicts a refractive index sensor device 1000 for analysing an analyst incorporating the refractive index sensor 100, 400 or 800 described hereinbefore according to exemplary embodiments of the present invention. In particular, the refractive index sensor device 1000 includes a refractive index sensor 100, 400, or 800 comprising a strip waveguide 104 and a slot waveguide 112, a light source (e.g., a broadband optical source) 1004 for outputting a light signal to the strip waveguide 104, and a detector (e.g., an optical spectrum analyzer (OSA)) 1008 for receiving the light signal from the strip waveguide 104 for analysis (preferably wavelength shift analysis) with respect to the analyte 108. The strip waveguide 104 is configured to receive the light signal therein from the light source 1004 and transmit the light signal, subject to manipulation as it propagates through the strip waveguide, to the detector 1008 for analysis. The slot waveguide 112 is configured for sensing the analyte disposed thereon and for receiving a sensing signal, corresponding to the above-mentioned manipulation of the light signal, from the strip waveguide 104. Furthermore, a grating 116 is formed on a surface of the strip waveguide 104 to enable coupling of the sensing signal from the strip waveguide 104 to the slot waveguide 112. In particular, the refractive index sensor 100, 400, or 800 is configured with enhanced sensitivity based on a sensitivity difference between the slot waveguide 112 and the strip waveguide 104, and/or a group index difference between the slot waveguide 112 and the strip waveguide 104.

Preferably, the refractive index sensor device 1000 further includes a polarization controller 1006 for receiving the light signal from the light source 1004, and outputting a TE polarized light signal to the strip waveguide.

Figure 11:
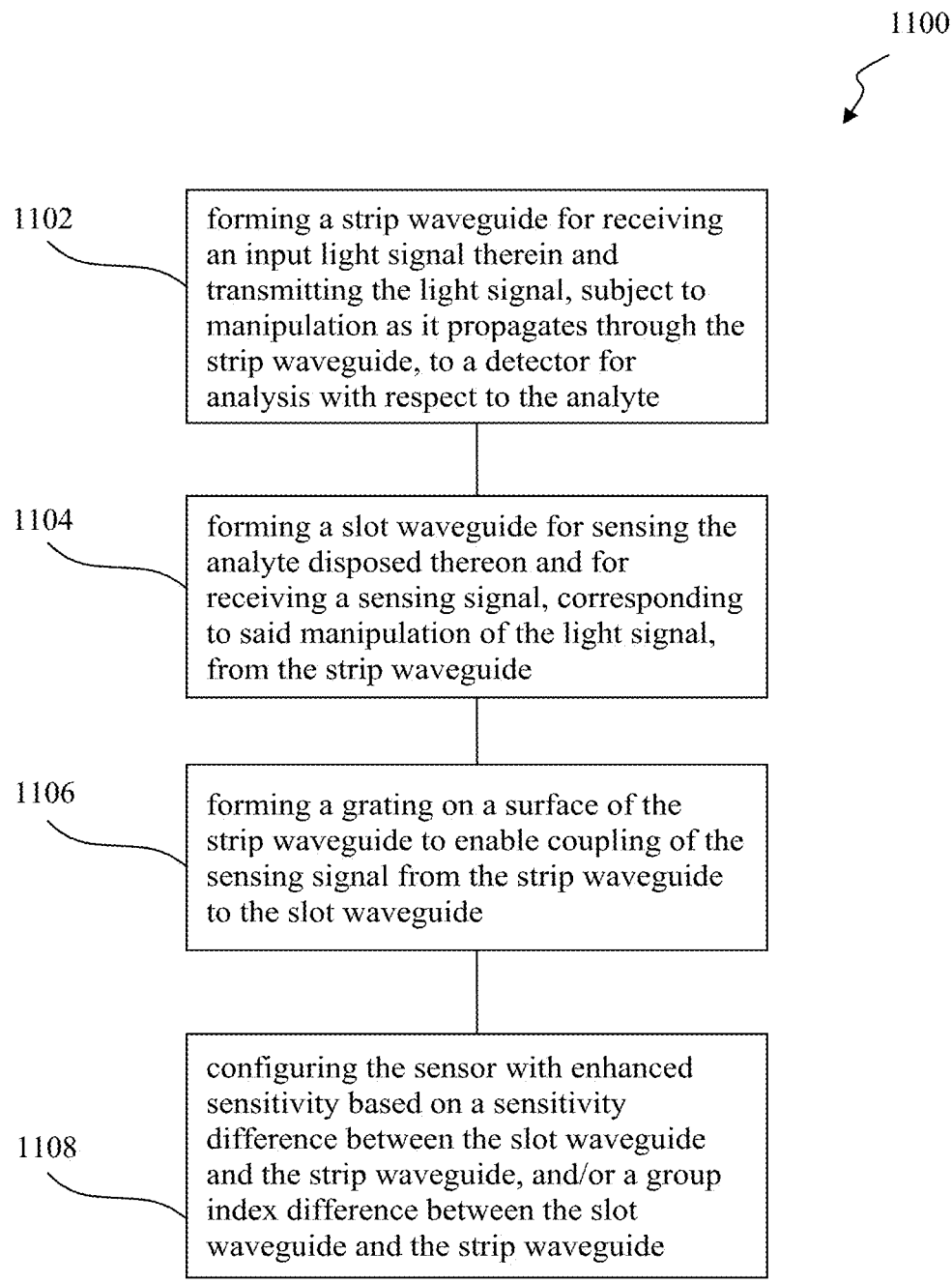
FIG. 11 depicts a flow chart generally illustrating a method of fabricating a refractive index sensor for analysing an analyte according to an embodiment of the present invention.

FIG. 11 depicts a flow chart generally illustrating a method 1100 of fabricating a refractive index sensor for analysing an analyte. The method 1100 includes a step 1102 of forming a strip waveguide for receiving an input light signal therein and transmitting the light signal, subject to manipulation as it propagates through the strip waveguide 104, to a detector (e.g., an optical spectrum analyser) 1008 for analysis with respect to the analyte 108, and a step 1104 of forming a slot waveguide 112 for sensing the analyte 108 disposed thereon and for receiving a sensing signal, corresponding to the above-mentioned manipulation of the light signal, from the strip waveguide 104. The method 1100 further includes a step 1106 of forming a grating on a surface of the strip waveguide to enable coupling of the sensing signal from the strip waveguide to the slot waveguide. It will be appreciated to a person skilled in the art that the above-described steps may be performed in any order and are not limited to the order presented. Furthermore, the above steps are not intended to be construed to necessitate individual steps and may be combined as one fabrication step where appropriate without deviating from the scope of the present invention.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A refractive index sensor for analysing an analyte, the sensor comprising:
a strip waveguide for receiving an input light signal therein and transmitting the light signal, subject to manipulation as it propagates through the strip waveguide, to a detector for analysis with respect to the analyte; and
a slot waveguide for sensing the analyte disposed thereon and for receiving a sensing signal, corresponding to said manipulation of the light signal, from the strip waveguide,
wherein a grating is formed on a surface of the strip waveguide to enable coupling of the sensing signal from the strip waveguide to the slot waveguide, and
the sensor is configured with enhanced sensitivity based on a sensitivity difference between the slot waveguide and the strip waveguide, and/or a group index difference between the slot waveguide and the strip waveguide.

2. The sensor according to claim 1, further comprises a substrate, wherein the strip waveguide and the slot waveguide are disposed on the substrate so as to be spaced apart and substantially parallel to each other.

3. The sensor according to claim 1, wherein the sensing signal is in the form of a light signal, and the grating has a grating period configured to couple light signal at a particular resonant wavelength from the strip waveguide to the slot waveguide.

4. The sensor according to claim 3, wherein the slot waveguide has a mode index which is subject to change based on the analyte disposed thereon, the change in the mode index results in a shift in the particular resonant wavelength of the light signal coupled from the strip waveguide to the slot waveguide, thereby enabling analysis of the analyte based on the shift in the particular resonant wavelength.

5. The sensor according to claim 3, wherein the sensor is configured such that its sensitivity (S) is determined based on the following equation:

$$S = \lambda_0 \frac{\Delta S}{\Delta N_g}$$

where, $\lambda_0$ is the particular resonant wavelength of the light signal, $\Delta S$ is the sensitivity difference between the slot waveguide and the strip waveguide, and $\Delta N_g$ is the group index difference between the slot waveguide and the strip waveguide.

6. The sensor according to claim 1, wherein the sensor is configured such that the sensitivity difference between the slot waveguide and the strip waveguide is increased and/or the group index difference between the slot waveguide and the strip waveguide is reduced.

7. The sensor according to claim 1, wherein the strip waveguide is isolated to decrease its sensitivity so as to increase the sensitivity difference between the slot waveguide and the strip waveguide.

8. The sensor according to claim 7, wherein the strip waveguide is enclosed by an isolation layer made of $SiO_2$ to isolate the strip waveguide from the analyte.

9. The sensor according to claim 7, wherein the strip waveguide is enclosed by an isolation layer made of a polymer material to isolate the strip waveguide from the analyte.

10. The sensor according to claim 9, wherein the polymer material has a thermal-optic coefficient selected for compensating a positive or negative temperature dependence of the sensor so as to reduce the temperature dependence of the sensor.

11. The sensor according to claim 10, wherein the polymer material is made of WIR30-490 or SU-8.

12. The sensor according to claim 1, wherein a width of the strip waveguide is configured to be about 600 nm to about 1000 nm.

13. The sensor according to claim 1, wherein one or more parameters of the slot waveguide are configured to increase its sensitivity so as to increase the sensitivity difference between the slot waveguide and the strip waveguide, said one or more parameters include a width of the slot waveguide and/or a width of a gap of the slot waveguide.

14. The sensor according to claim 13, wherein the slot waveguide is configured such that the width of the slot waveguide is increased and/or the width of the gap is reduced.

15. The sensor according to claim 13, wherein the width of the slot waveguide is in the range of about 350 nm to about 550 nm, and the width of the gap is in the range of about 50 nm to about 300 nm.

16. The sensor according to claim 1, wherein a plurality of gratings, spaced apart from each other, is formed on the surface of the strip waveguide, each grating having a different grating period configured for coupling a sensing signal at a respective resonance wavelength to the slot waveguide, thereby enabling wavelength multiplexed measurement.

17. The sensor according to claim 1, wherein the slot waveguide and/or the strip waveguide are made of silicon nitride ($Si_3N_4$).

18. A method of fabricating a refractive index sensor for analysing an analyte, the method comprising:
forming a strip waveguide for receiving an input light signal therein and transmitting the light signal, subject to manipulation as it propagates through the strip waveguide, to a detector for analysis with respect to the analyte; and
forming a slot waveguide for sensing the analyte disposed thereon and for receiving a sensing signal, corresponding to said manipulation of the light signal, from the strip waveguide,
wherein the method further comprises forming a grating on a surface of the strip waveguide to enable coupling of the sensing signal from the strip waveguide to the slot waveguide, and
configuring the sensor with enhanced sensitivity based on a sensitivity difference between the slot waveguide and the strip waveguide, and/or a group index difference between the slot waveguide and the strip waveguide.

19. A refractive index sensor device for analysing an analyte, the sensor device comprising:
a refractive index sensor comprising a strip waveguide and a slot waveguide;
a light source for outputting a light signal to the strip waveguide; and a detector for receiving the light signal from the strip waveguide for analysis with respect to the analyte;

wherein the strip waveguide is configured to receive the light signal therein from the light source and transmit the light signal, subject to manipulation as it propagates through the strip waveguide, to the detector for analysis, the slot waveguide is configured for sensing the analyte disposed thereon and for receiving a sensing signal, corresponding to said manipulation of the light signal, from the strip waveguide, a grating is formed on a surface of the strip waveguide to enable coupling of the sensing signal from the strip waveguide to the slot waveguide, and the refractive index sensor is configured with enhanced sensitivity based on a sensitivity difference between the slot waveguide and the strip waveguide, and/or a group index difference between the slot waveguide and the strip waveguide.

20. The refractive index sensor device according to claim 19, further comprising a polarization controller for receiving the light signal from the light source, and outputting a TE polarized light signal to the strip waveguide.

* * * * *